United States Patent [19]

Gittos et al.

[11] Patent Number: 5,011,846

[45] Date of Patent: Apr. 30, 1991

[54] MEDICAMENT COMPOSITIONS DERIVED FROM QUINOLIZINE AND QUINOLIZINONE AND METHODS OF USE THEREOF

[75] Inventors: Maurice W. Gittos, Plobsheim, France; Francis P. Miller, Loveland; Stephen M. Sorensen, Cincinnati, both of Ohio; John R. Fozard, Hegenheim; Paul Moser, Strasbourg, both of France; Michael G. Palfreyman; Hsien Cheng, both of Cincinnati, Ohio

[73] Assignee: Merrell Dow Pharmaceuticals Inc., Cincinnati, Ohio

[21] Appl. No.: 527,676

[22] Filed: May 16, 1990

Related U.S. Application Data

[63] Continuation of Ser. No. 313,119, Feb. 21, 1989, abandoned.

[30] Foreign Application Priority Data

Feb. 23, 1988 [FR] France .............................. 88 400415
Feb. 23, 1988 [FR] France .............................. 88 400418
Feb. 23, 1988 [FR] France .............................. 88 400416
Feb. 23, 1988 [FR] France .............................. 88 400417
Jan. 11, 1989 [FR] France .............................. 89 100392

[51] Int. Cl.$^5$ ............................................. A61K 471/18
[52] U.S. Cl. ................................................... 514/294
[58] Field of Search ........................................... 514/294

[56] References Cited

FOREIGN PATENT DOCUMENTS 0220011 7/1986 European Pat. Off. .
0266730 5/1988 European Pat. Off. .
2145416 8/1984 United Kingdom .
2152049 12/1984 United Kingdom .

OTHER PUBLICATIONS

Hyperactivity Following Withdrawal of Mesolimbic Dopamine Infusion and Neuroleptic Treatment is Reversed by GR380231, *British Journal of Pharmacology*, vol. 91, p. 338 P, (1987).

More on Beecham's 5HT Compounds, Scrip, No. 1193, p. 28, (Apr. 3rd 1987).

Increased Gut Cholinergic Activity and Antagonism of 5-Hydroxytryptamine M-Receptors by BRL 24924; Potential Clinical Importance of BRL 24924: Potential clinical Importance of BRL 24924, *Br. J. pharmac.*, vol. 91, p. 77 (1987).

Effects of the 5HT$_3$ Receptor Antagonists, GR 3803F, on Raised Dopaminergic Activity in the Mesolimibic System of the Rat and Marmoset Brain, *British Journal of Pharmacology*, vol. 92, pp. 881-894, (1987).

Research, High Hopes for Glaxo Drug, but Early Days Yet, *The Pharmaceutical Journal*, p. 14, Jan. 3, 1987.

Anxiogenesis Follows Abstinence Withdrawal from Long-Term Treatment with Diazepam but not GR 38032F, *British Journal of Pharmacology*, vol. 90, p. 420 P, (Mar. 1987).

The Anxiolytic Activities of GR 38032F, A 5HT$_3$ Receptor Antagonists, in the Rat and Cynomolgus Monkey, *British Journal of Pharmacology*, vol. 90, p. 88P, (Mar. 1987).

The Anxiolytic Activities of 5HT$_3$ Antagonists in Laboratory Annimals, *Neuroscience Letter*, Supp. 29, p. S 68, (1987).

The Antipsychotic Potential of GR 38032F, a Selective 5HT$_3$ Antagonist, *Neuroscience Letter*, Supp. 29, p. S 69 (1987).

*Primary Examiner*—David B. Springer
*Attorney, Agent, or Firm*—J. Michael Dixon

[57] ABSTRACT

The present invention is directed to the use of esters of hexahydro-8-hydroxy-2,6-methano-2H-quinolizin-3(4H)-one and hexahydro-8-hydroxy-2,6-methano-2H-quinolizines in the manufacture of a medicament for the treatment of anxiety, psychosis, glaucoma and for the stimulation of gastric motility.

15 Claims, No Drawings

MEDICAMENT COMPOSITIONS DERIVED FROM QUINOLIZINE AND QUINOLIZINONE AND METHODS OF USE THEREOF

CROSS-REFERENCE TO RELATED APPLICATION

This is a continuation of application Ser. No. 313,119, filed Feb. 21, 1989, abandoned.

The present invention relates to the use of quinolizine and quinolizinone derivatives in the manufacture of a medicament for the treatment of anxiety, psychosis, glaucoma, and to stimulate gastric motility. The invention also relates to certain novel derivatives of quinolizine and quinolizinone which are useful for the purposes indicated above and which are also useful for the treatment of migraine and the treatment of nausea and vomiting.

In accordance with the present invention, it has been discovered that anxiety, glaucoma, and psychosis can be treated and that gastric motility can be stimulated, in a patient in need thereof, by the administration of an effective amount of a compound of the formula:

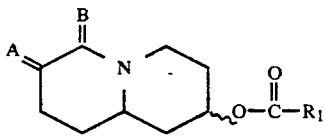

Formula I wherein A is $H_2$, O, (H)(OH), $(OH)_2$ or N-OH; B is $H_2$, (H)($CH_3$), (H)($CH_2NR_3R_4$) or $CH_2$ wherein $R_3$ and $R_4$ are $C_{2-4}$ alkyl or are combined to give tetramethylene, pentamethylene or —$CH_2CH_2$—O—$CH_2CH_2$—; $R_1$ is

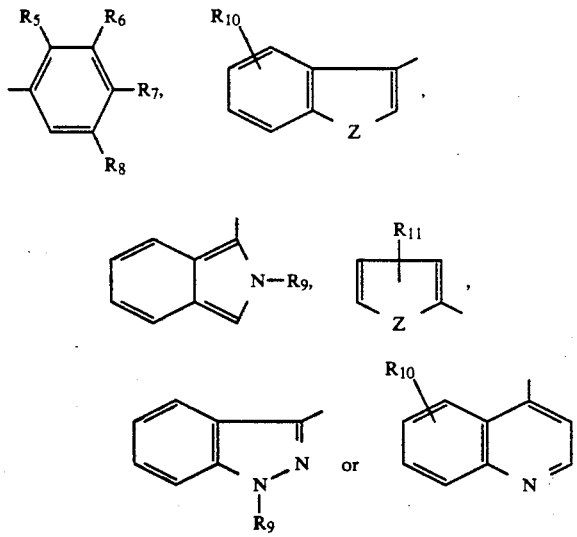

wherein Z is $NR_9$, O or S; $R_5$, $R_6$, and $R_8$ are each hydrogen, halogen, $C_{1-3}$ alkyl or $C_{1-3}$ alkoxy; $R_7$ is hydrogen, amino, ($C_{1-4}$ alkyl)amino, ($C_{1-4}$ alkyl)$_2$amino, alkoxy or nitro; $R_9$ is hydrogen, $C_{1-4}$ alkyl or phenyl ($C_{1-2}$ alkyl); $R_{10}$ is hydrogen, halogen $C_{1-4}$ alkyl, $C_{1-4}$ alkoxy, hydroxy, cyano or —$CONH_2$; indicates that the configuration of the oxygen substituent on the ring can be endo or exo; and the pharmaceutically acceptable acid addition and quaternary ammonium salts of the aforesaid compounds.

A novel group of compounds, according to the present invention are compounds of the following formula:

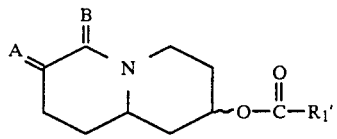

Formula II wherein $R_1'$ is

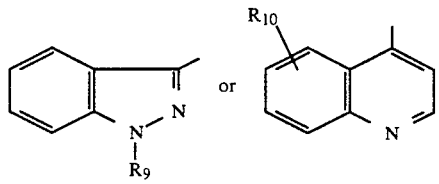

and A, B, $R_9$ and $R_{10}$ are defined as above.

Examples of the $C_{1-4}$ alkyl groups referred to above are methyl, ethyl, propyl, isopropyl and butyl. Examples of the $C_{1-4}$ alkoxy groups are methoxy, ethoxy, propoxy and butoxy. The halogens referred to above can be fluorine, chlorine or bromine. When the wavy line in the general structural formula is changed to a solid line, this indicates that the configuration of the compounds is endo. Such endo-compounds can also be referred to as trans. Similarly, exo-compounds can also be referred to as cis. Any hydrates of the present compounds are considered as equivalent to the compounds themselves and this would include compounds in which the carbonyl (i.e., A is O) exists as $(OH)_2$.

A preferred group of compounds for use in the present invention are those wherein the ester is attached to the polycyclic ring in the endo-configuration. A further preferred group are those having the endo-configuration wherein A is =O and =$(OH)_2$. In a still further preferred group, B is additionally =$H_2$.

The pharmaceutically acceptable acid addition salts referred to above can be non-toxic salts with suitable acids such as those with inorganic acids, for example hydrochloric, hydrobromic, nitric, sulfuric or phosphoric acids; or with organic acids such as organic carboxylic acids, for example, acetic, propionic, glycolic, maleic, hydroxymaleic, malic tartaric, citric, salicyclic, 2-acetyloxybenzoic, nicotinic or isonicotinic; or organic sulfonic acids, for example methanesulfonic, ethanesulfonic, 2-hydroxyethanesulfonic, 4-toluenesulfonic or 2-naphthalensulfonic. Quaternary ammonium salts are formed with alkyl halides such as methyl chloride, methyl bromide or ethyl bromide; or with sulfate esters such as methyl 4-toluenesulfonate or methyl 2-naphthalenesulfonate.

Some specific examples of compounds encompassed by the present invention are the following:

endo-8-(3,5-Dimethylbenzoyloxy)hexahydro-2,6-methano-2H-quinolizin-3(4H)-one exo-8-(3,5-Dimethylbenzoyloxy)hexahydro-2,6-methano-2H-quinolizin-3(4H)-one endo-8-(3,5-Dichlorobenzoyloxy)hexahydro-2,6-methano-2H-quinolizin-3(4H)-one endo-8-(3,5-Dimethoxybenzoyloxy)hexahydro-2,6-methano-2H-quinolizin-3(4H)-one endo-8-(4-Aminobenzoyloxy)hexahydro-2,6-methano-2H-quinolizin-3(4H)-one endo-8-(4-Dimethylaminobenzoyloxy)hexahydro-2,6-methano-2H-quinolizin-3(4H)-one endo-8-(3,5-Dimethylbenzoyloxy)octahydro-2,6-methano-2H-quinolizine endo-8-(3-Indolylcarbonyloxy)octahydro-2,6-methano-2H-quinolizine endo-8-(5-Cyano-3-indolylcarbonyloxy)hexahydro-2,6-methano-2H-quinolizin-3(4H)-one endo-8-(3,5-Dichlorobenzoyloxy)hexahydro-2,6-methano-4-methyl-2H-quinolizin-3(4H)-one endo-8-(3-Indolylcarbonyloxy)hexahydro-4-(diethylaminomethyl)-2,6-methano-2H-quinolizin-3(4H)-one endo-8-(3-Indolylcarbonyloxy)-3-hydroxyimino-2,6-methanooctahydro-2H-quinolizine endo-8-(2-Methyl-1-isoindolycarbonyloxy)hexahydro-2,6-methano-2H-quinolizin-3(4H)-one endo-8-(2-Pyrrolidinylcarbonyloxy)hexahydro-2,6-methano-2H-quinolizin-3(4H)-one endo-8-(3-Indolylcarbonyloxy)-2,6-methanooctahydro-2H-quinolizin-3-ol endo-Hexahydro-8-(1-methyl-3-indazolylcarbonyloxy)-2,6-methano-2H-quinolizin-3(4H)-one endo-Hexahydro-8-(3-indazolylcarbonyloxy)-2,6-methano-2H-quinolizin-3(4H)-one.

The compounds of the present invention can be prepared by reacting an alcohol or a reactive derivatives thereof, said alcohol having the formula:

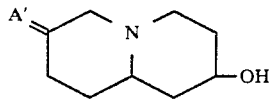

wherein A' is O or $H_2$, with a reactive equivalent of an acid of the formula:

$R_1COOH$ wherein $R^1$ is defined as above. By a reactive equivalent of the acid is meant the corresponding acid chloride or bromide or the corresponding glyoxylyl chloride or bromide or the carboxylic acid imidazole obtained by the reaction of the appropriate acid halide with N,N-carbonyldiimidazole; or any similar acid derivative which would yield the simple carboxylic acid ester on reaction with an alcohol or with a reactive derivative of an alcohol. More specifically, where the —OH in the alcohol is equatorial (exo), then it can be reacted with the appropriate carboxylic acid imidazole obtained by the reaction of the acid halide with N,N-carbonyldiimidazole. Alternatively, the acid can be converted to the acid chloride by standard procedures (e.g., thionyl chloride) and then reacted with the alcohol or an alkali metal salt of the alcohol such as the lithium salt obtained by the reaction of lithium hydride with the alcohol in tetrahydrofuran.

When the —OH group in the starting alcohol is axial (endo), it can also be converted to the corresponding ester by reaction with the appropriate acid chloride or bromide with the reaction being carried out in the presence of an equivalent of a suitable tertiary base such as 4-dimethylaminopyridine in a high boiling inert solvent such as xylene. In this case, however, long heating (24-84 hours) at a temperature at or above 140° C. is necessary so that the procedure would not be suitable for use with acid halides that are not stable under the indicated conditions. Thus, it was necessary to use an alternative for the preparation of such compounds. In this procedure, an appropriate acid chloride or bromide or a glyoxylyl chloride or bromide, in a nitroparaffin solvent, is reacted with a solution of a super acid salt of the alcohol and an equivalent amount of a heavy metal salt of the same super acid. The glyoxylyl chloride can be used in the process as indicated because it decarbonylates readily under the conditions used. The reaction itself can be carried out over a period of 1-24 hours at temperatures ranging from −80° C. to ambient temperatures (about 23° C.). Examples of suitable super acids with M=H are $MBF_4$, $MAsF_6$, $MSbF_6$, $MPF_6$, $MTaF_6$ or $MNbF_6$ with examples of suitable heavy metals (M) being silver and thallium. Examples of nitroparaffin solvents are nitromethane, nitroethane, 1-nitropropane and 2-nitropropane.

Actually, where the group $R_1$ contains a primary or secondary amino group, it is usually protected during the above reaction, with a benzyl group being commonly used to protect a secondary amine and a benzyloxycarbonyl group being used to protect a primary amine. In either case, the protecting group in the product is removed by conventional procedures, for example by hydrogenation with hydrogen and a palladium catalyst.

Various procedures can be used to convert those compounds wherein A is O and whose preparation is described below, to other different bridged derivatives of the present invention by standard methods. Thus, the ketone group in the polycyclic system can be reduced to the corresponding alcohol using an alkali metal (sodium or potassium) borohydride in a lower alkanol such as methanol or ethanol.

The ketone group can also be reduced completely to a methylene group by a two step procedure. In the first step, the ketone is reacted with ethylene dithiol or trimethylene dithiol in the presence of a strong acid such as hydrochloric acid or $BF_3$ to give the corresponding dithioketal. The reaction is carried out in a suitable polar solvent such as nitromethane or acetic acid. The dithioketal is then reduced with hydrazine in the presence of Raney nickel in a lower alkanol solvent such a 2-propanol at elevated temperatures (60°-100° C.). Actually this same procedure can be used to reduce the original starting alcohol, hexahydro-8-hydroxy-2,6-methano-2H-quinolizin-3(4H)-one, to 8-hydroxy-2,6-methanooctahydro-2H-quinolizine which can itself be reacted with acid derivatives as described earlier to give the corresponding esters.

Compounds containing other B-groups (i.e. aminomethyl, methylene or methyl groups) can be obtained from products in which A is O and B is $H_2$ by a Mannich reactions using formaldehyde and a secondary amine such as dimethylamine, diethylamine, piperidine or pyrrolidine. This reaction gives the corresponding aminomethyl compound and, when B is dimethylaminomethyl, the amino moiety is eliminated on heating at 90°-110° C. in an inert solvent such as toluene to give the corresponding methylene compound (B is =CH$_2$). This exocyclic methylene compound can be isolated by standard methods and transformed into a methyl group by hydrogenation, for example, by using hydrogen and platinum oxide.

To obtain those compounds in which A is hydroxyimino (N—OH), the ketone referred to above can be reacted with hydroxylamine hydrochloride by standard procedures.

The alcohol used as a reactant in the above procedure can be obtained from known alkyl ($C_{1-4}$) 3-cyclopentene-1-carboxylates by a multi-step procedure. Specifically, the double bond in the indicated cyclopentene is oxidized to a 1,2-diol using N-methylmorpholine N-oxide in the presence of osmium tetroxide catalyst. The diol is then cleaved to the corresponding dialdehyde using sodium metaperiodate. A Robinson-Schöpf cyclization of the dialdehyde with a lower alkyl glycine ester and acetone-dicarboxylic acid, preferably at pH 4, gives a pseudopelletierine derivative of the following type:

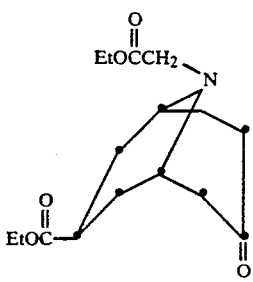

The ketone group is reduced to an alcohol using sodium borohydride and the product is reacted with dihydropyran to protect the —OH group as a tetrahydropyranyl ether. Dieckmann cyclization of the diester using a strong base (e.g. potassium t-butoxide) followed by aqueous acid hydrolysis and decarboxylation gives the desired alcohol. The resulting alcohols can exist in two conformations—axial and equatorial. The main product obtained by the above procedure is the axial alcohol and it can be separated from the equatorial isomer by crystallization of the camphorsulfonate or tetrafluoroborate salt.

The compounds represented by Formula I are 5-HT M-receptor antagonists. The 5-HT M-receptor is also known as the 5HT-3 receptor to those skilled in the art. The compounds are useful in the treatment of anxiety, glaucoma, and psychosis and in the manufacture of a medicaments, therefor. The compounds are also useful for increasing gastric motility and in the manufacture of medicaments, therefor.

The activity of the compounds against 5-HT can be assessed by determining their $pA_2$ values in the isolated rabbit heart as described by J. R. Fozard et al., Eur. J. Pharmacol., 59, 195–210 (1979). In the method described, the molar concentration of antagonist which reduces the effects of twice the $ED_{50}$ of 5-HT to that of the $ED_{50}$ in the absence of antagonist is determined. The $pA_2$ value is the negative logarithm of said molar concentrations. In general terms, the higher the $pA_2$ value the more potent is the compound. When tested in this way, the present compounds show $pA_2$'s generally in the range of about 8 to 10.

The activity of these compounds against 5-HT can be assessed in vivo by measurement of the effect of the compound on the Von Bezold-Jarisch Reflex induced by 5-HT injected intravenously into the rat (see Paintal A.S., Physiol. Rev. 53, 159–227, 1973; J. R. Fozard, Naunyn-Schmiedeberg's Arch. Pharmacol., 326, 1984, 36–44). The transient cardiac slowing arises from an increased afferent vagus activity arising from stimulation by 5-HT of sensory afferent fibers in and around the heart. When tested against the Von Bezold-Jarisch Reflex induced by 5-HT, compounds endo-8-(3,5-dimethylbenzoyloxy)hexahydro-2,6-methano-2H-quinolizin-3(4H)-one hydrochloride and endo-hexahydro-8-(3-indolylcarbonyloxy)-2,6-methano-2H-quinolizin-3(4H)-one hydrochloride suppressed the response dose-dependently at doses of 0.01–0.1 mg/kg given intravenously or 0.25–1 mg/kg given orally.

The present compounds appear to be highly selective in their action against the 5-HT M-receptor. Their potency against other 5-HT receptors and other spasmogens, in particular carbachol, phenylephrine, histamine and calcium, is known to be at least three orders lower that that against 5-HT M-receptors.

As used in this application:

(a) the phrase "gastric motility", refers to the rate at which the stomach empties its contents into the duodenum.

(b) the term "glaucoma" refers to a group of eye diseases characterized by an increase in intraocular pressure, which can cause pathological changes in the optic disk and typically defects in the field of vision.

(c) the term "intraocular pressure" refers to the pressure within the eyeball.

(d) the term "anxiety" refers to a condition where a patient is experiencing fear, apprehension, uncertainty, etc., and can be accompanied with physical manifestations such as, tachycardia, tremors, sweating, etc.

(e) the term "psychosis" refers to a condition where the patient, e.g., a human, experiences a major mental disorder of organic and/or emotional origin characterized by derangement of the personality and loss of contact with reality, often with delusions, hallucinations or illusions, such as, for example, schizophrenia or mania.

(f) the term "treatment" refers to the ability to either relieve or alleviate the patient's disease.

(g) the term "patient" as used herein is taken to mean warmblooded animals, such as mammals, for example, dogs, rats, mice, cats, guinea pigs, horses, cattle, sheep and primates, including humans.

The compounds of Formula I exhibit the pharmacological action of increasing the motility of the upper gastrointestinal tract. This means that the compounds increase the rate at which the stomach empties its contents into the duodenum.

Thus, the compounds are useful in the treatment of gastric stasis. Gastric stasis refers to a condition where the stomach's ability to empty its contents into the duodenum is impaired. This typically produces discomfort in the patient.

The compounds are also useful in the treatment of gastroesophageal reflux. Gastroesophageal reflux refers to a condition, where small quantities of gastric juice are refluxed into the lower part of the esophagus. The acidic gastric juice irritates the mucosa of the esophagus causing pain and discomfort in the patient.

The quantity of compound required to produce this gastric motility stimulating effect described above will vary with the particular compound utilized, the patient, the route of administration, the severity of the patient's condition, the presence of other underlying disease states in the patient, and other medications which are being administered concurrently to the patient. Generally though, a patient will respond to dosage range of from 0.01 to 10 mg/kg/day.

One method of demonstrating that the compounds of Formula I increase gastric motility is the following test protocol. Male mice should be fasted overnight prior to being utilized in the test. One group of mice should be administered saline intraperitoneally, and the other group should be administered a compound of Formula I such as, for example, endo-hexahydro-8-(3-indolylcarbonyloxy)-2,6-methano-2H-quinolizin-3(4H)-one, at a dose of 5 mg/kg intraperitoneally in a saline carier.

One hour after administration of either the drug or a saline control, the mice should be given 0.3 ml intragastrically of a suspension containing 10% w/v charcoal, and 5% w/v tragacanth gum with the aid of a feeding needle. Fifteen minutes later the animals should be sacrificed.

The stomachs should be surgically removed and then weighed. The contents should be washed from the stomach, and then the stomachs should be reweighed. The groups should then be compared utilizing the change in weight of the stomach after washing, as an indicator of the rate of gastric emptying.

As noted above, the compounds are also useful as antipsychotics. The quantity of compound required to produce this antipsychotic therapeutic effect will vary with the particular compound utilized, the patient, the severity of the patients illness, the presence of other disease states within the patient, and the mode of administration. Generally though, a patient's psychosis will respond to the compound at a dosage range at from about 0.01 mg/kg to about 10 mg/kg of patient body weight per dosage.

The compounds of Formula I are not dopamine antagonists. Therefor, patients being administered one of these compounds will not experience the numerous side effects that are typically associated with the neuroleptic agents that are currently available, such as chlorpromazine, haloperidol, fluphenazine, etc.

One manner of demonstrating the antipsychotic utility of these compounds is by their ability to block the hyperactivity which usually accompanies the intra-accumbens administration of amphetamine in rats. The following test protocol can be utilized to demonstrate this activity.

This pharmocological effect is measured indirectly. This is accomplished by measuring what effect the compound has upon the ability of a rat to avoid an electrical shock, which it has previously learned to avoid. Initially, the rat should be placed in a test chamber capable of delivering an electrical shock to the rat at a specified rate, for example once every 20 seconds. The test chamber should also be capable of delaying the rate at which electrical shocks are administered if the rat performs the proper avoidance behavior, such as moving from one side of the chamber to the other. The rat should be repeatedly exposed to this test chamber on a regular basis until it has learned to consistently engage in the behavior which delays the response. After it has learned this behavior it is suitable for further testing.

A bilateral cannulae should be implanted in the nucleus accumbens according to the following procedure. The rat should be anesthetized and mounted in a stereotaxic device. A small hole is drilled thru the skull at coordinates A1.5, L1.4[1] (relative to bregma), bilaterally and an additional hole is drilled near by for a small machine screw. A 20 gauge cannulae is placed stereotaxically, so as to terminate 1 mm above, the nucleus (V6.0, brain surface)[1]. Dental acrylic can be utilized to secure the cannulae to the anchor screw and a 25 gauge stylus can be utilized as a plug for each cannulae.

[1]Paxino G. and Watson L., "The Rat Brain in Stereotazic Coordinates", 2nd Ed.,m Academic Press, 1986.

At least seven days after surgery, the rat should be exposed to the electrical stimuli in the test chamber in order to ascertain that it can still engage in the behavior which delays the rate at which shocks are administered. Rats demonstrating this avoidance response are suitable for use in the comparative tests.

The rat should be administered intra-accumbens amphetamine (10 mcg/side), subjected to electrical shock in the test chamber and its rate of avoidance recorded.

Thereafter, the rat can be administered the test compound (0.25 ng/side) via the intra-accumbens cannulae. Thirty minutes after administration of the test compound, the rat should be administered intra-accumbens amphetamine (10 mcg/side), subjected to electrical shock in the test chamber and its rate of avoidance recorded.

Rats administered amphetamine alone will exhibit an increased rate of avoidance. Rats administered both amphetamine and a compound of Formula I, such as for example, endo-hexahydro-8-(3-indolylcarbonyloxy)-2,6-methano-2H-quinolizin-3(4H)-one will not exhibit this increased rate of avoidance.

The compounds of the present invention exhibit the pharmacological activity of lowering intraocular pressures. Thus, these compounds are useful in the treatment of glaucoma.

The compounds can be administered via ophthalmic dosage forms such as, for example, ophthalmic drops, ophthalmic ointments, and ophthalmic disks. The ophthalmic drops of the present invention should contain from 0.1-10% w/w of one of the compounds of Formula I. Typically, it will be dissolved in a buffered, isotonic solution containing antimicrobial preservative agents. The ophthalmic ointments will also generally contain from 0.1-10% w/w of one of the compounds of Formula I admixed with a suitable base, such as white petrolatum and mineral oil, along with antimicrobial preservatives. The ophthalmic disks will typically be constructed so as to contain a core of active ingredient surrounded by a polymer matrix such as, for example, a hydrophobic ethylene/vinyl acetate copolymer. Specific methods of compounding these dosage forms, as well as appropriate ophthalmic pharmaceutical carriers are known in the art. REMINGTON PHARMACEUTICAL SCIENCES, 16th Ed. Mack Publishing Co. (1980).

Typically, the ophthalmic drops or ophthalmic ointments will be administered from 1 to 4 times daily. The ophthalmic disks will be administerd weekly.

If desired, the compounds of Formula I can be administered systemically in order to lower intraocular pressures. The quantity of compound required to produce this ocular hypotensive effect as the result of systemic administration will vary with the particular compound utilized, the patient, the route of administration, the severity of the patient's glaucoma, the presence of other underlying disease states in the patient, and other medications which are being administered concurrently to the patient. Generally though, a patients glaucoma will respond to dosage range of from 0.01 to 10 mg/kg/day, if administered systemically.

The compounds of Formula I are useful in the treatment of anxiety; that is relieving or alleviating the apprehension, fear, or uncertainty, etc., that patients suffering from anxiety commonly experience, as well as relieving or alleviating the physiological changes associated with anxiety such as tachycardia, tremors, sweating, etc.

The compounds of Formula I possess a significant advantage over the anxiolytic agents which are currently available to clinicians, such as chlordiazepoxide, diazepam, and other benzodiazepines. The benzodiazepines commonly cause sedation and impairment of motor skills at the dosage levels commonly used in the treatment of anxiety.

The compounds of Formula I do not suffer from this disadvantage. They exhibit a wide dosage range at which they demonstrate anxiolytic activity, without causing either sedation or impairment of motor skills.

The quantity of compound required to produce the anxiolytic effect described above will vary with the particular compound utilized, the patient, the route of administration, the severity of the patient's anxiety, the presence of other underlying disease states in the patient, and other medications which are being administered concurrently to the patient. Generally though, a patient's anxiety will respond to dosage range of from 0.01 to 10 mg/kg/day.

The novel compounds of Formula II are further useful for the treatment of pain, especially migraine, vascular and cluster headaches and trigeminal neuralgia. They are also useful in the treatment of nausea and vomiting arising from treatment with cancer chemotherapeutic agents.

In the past, acute attacks of migraine have been treated with a peripheral vasoconstrictor, such as ergotamine, which may be co-administered with caffeine, and dihydroergotamine; an antipyretic analgesic, such as acetylsalicylic acid or p-acetylaminophenol; and/or an antiemetic such as cyclizine, metoclopramide and thiethylperazine. It has also been reported (J. B. Hughes, Med. J. Aust. 2, No. 17, 580 (1977)) that immediate relief of an acute migraine attack can be obtained by slow intravenous injection of metoclopramide (10 mg).

It is believed that 5-hydroxytryptamine (5-HT) is the naturally occurring substance most likely to play a role in the pathophysiology of migraine. Increased amounts of 5-HT and its metabolite 5-hydroxyindoleacetic acid are excreted in the urine during most attacks. Further, plasma and platelet 5-HT concentrations fall rapidly at the onset of an attack and remain low while the headache persists. Moreover, attacks of migraine have been clearly associated with periods of thrombocytopaenia in certain patients. It has been proposed that compounds which block the activity of 5-HT would be of use in the symptomatic treatment of migraine (J. R. Fozard, International Headache Congress 1980, reported in *Advances in Neurology*, Vol 33., Raven Press, New York, 1982).

The known migraine prophylactic drugs, methysergide, propranolol, amitriptyline, and chlorpromazine have widely different pharmacological activities but all are 5-HT D-receptor antagonists at the doses used clinically for the prophylaxis of migraine. Metoclopramide is a potent 5-HT M-receptor antagonist and it has been proposed (J. R. Fozard supra) that a blockade of the M-receptor present on afferent sensory neurones affords symptomatic relief in an acute migraine attack.

The potency as 5-HT receptor antagonists of (−) cocaine and some related compounds, including pseudotropyl benzoate (i.e., benzoylpseudotropine) and 3,5-dichlorobenzoyltropine has been reported (J. R. Fozard et al., *Eur. J. Pharmacol.*, 59, (1979) 195–210; J. R. Fozard, *Naunyn-Schmiedeberg's Arch Pharmacol.*, 326, (1984), 36–44). The pA$_2$ values reported for metoclopramide, pseudotropyl benzoate, nor (−) cocaine and benzoyltropine are 7.2, 7.0, 7.7, and 7.2 respectively whilst the pA$_2$ value determined for 3,5-dichlorobenzoyltropine by the same procedure is 9.3 (J. R. Fozard et al., *Eur. J. Pharmacol.*, 49, (1978) 109–112; J. R. Fozard, *Naunyn-Schmiedeberg's Arch Pharmacol.*, 326, (1984), 36–44). In a double-blind clinical trial, 3,5-dichlorobenzoyltropine proved an effective treatment for the acute migraine attack (C. Loisy et al., *Cephalalgia*, 5, (1985) 79–82). A further series of tropine esters, with pA$_2$ values for blockade of the 5-HT M-receptors between 7.7 and 13.6 have been described by Richardson et al., *Nature*, 316, (1985) 26–131.

The compounds of Formula II of the present invention block the M-receptors for 5-hydroxytryptamine (5-HT) on afferent sensory neurones, certain of which subserve the transmission of pain. As explained above, the blocking of such M-receptors appears to be a mechanism whereby the symptoms of migraine can be relieved. Accordingly, the compounds are useful in the treatment of migraine when administered in amounts sufficient to effectively block the said M-receptors.

In addition, compounds blocking 5-HT M-receptors, including metoclopramide, 3,5-dichlorobenzoyltropine and (3α-tropanyl)-1H-indole-3-carboxylic acid ester, are highly effective in preventing the nausea and vomiting induced by cancer chemotherapeutic agents in an animal experimental model (W. D. Miner et al., *Brit. J. Pharmacol.*, 88, (1986) 374P; W. D. Miner and G. J. Sanger, *Brit J. Pharmacol.*, 88, (1986) 497–499; B. Costall et al., *Neuropharmacology*, 25, (1986) 959–961). It is believed that cytotoxic drug-induced vomiting involves a 5-HT M-receptor mechanism (W. D. Miner and G. J. Sanger, *Brit J. Pharmacol.*, 88, (1986) 497–499). Accordingly, the compounds of Formula II are useful in the treatment of cytotoxic drug-induced vomiting when administered in amounts sufficient to effectively block the said M-receptors.

The dosage range at which the compounds of Formula II exhibit their anti-migraine and anti-emetic effects will vary depending upon the particular compound utilized, the patient, the route of administration, the severity of the patient's condition, the presence of other underlying disease states in the patient, and other medications which are being administered concurrently to the patient. Generally though, a patient's condition will respond to a dosage range of from 0.01 to 10 mg/kg/day.

The compounds of Formula I can be administered in various manners to achieve the desired effect. The compounds are typically administered either orally or parenterally (subcutaneously, intravenously, intramuscularly). They can also be administered by suppository. As noted above, opthalmic preparations may also be utilized when glaucoma is being treated.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc. as are known in the art.

The following examples are presented in order to further illustrate the compounds used in the present invention. However, they should not be construed as limiting the scope of the invention in any manner. These compounds are disclosed and claimed in European Patent Application 87116119.6.

EXAMPLE 1

To a stirred solution of 160 g of diethyl malonate in 1.5 l of dry dimethylformamide at 0° C. under nitrogen was slowly added 30 g of lithium hydride. After the evolution of hydrogen ceased (2 hours) 143 g of cis-1,4-dichloro-2-butene was slowly added and the mixture allowed to come to room temperature. After 72 hours, the mixture was diluted with a mixture of ether and hexane (1:4) and poured into water. The organic layer was washed with water and brine before drying over magnesium sulfate. Distillation gave diethyl 3-cyclopentene-1,1-dicarboxylate, bp 70°–80° C./0.1 mm, containing a small amount (~10%) of diethyl 2-vinylcyclopropane-1,1-dicarboxylate.

The impure cyclopentene diester (148.5 g) obtained above was added to a solution of 118 g of potassium hydroxide in 1333 ml of 80% ethanol and the stirred solution warmed at 60°–70° C. overnight. The ethanol was evaporated and the residue treated with an ice cold solution of concentrated sulphuric acid (107 ml) in water (274 ml). Extraction of the acid mixture with ether (3×400 ml) followed by evaporation of the dried ether extracts gave a residue of the diacid which was decarboxylated to the monoacid by heating in an oil bath at 170°–180° C. for 1 hour. The residual oil was distilled to give crude 3-cyclopentene-1-carboxylic acid, bp 68°–73° C. (1 mm) containing some γ-vinyl-γ-butyrolactone. A solution of 98 g of potassium carbonate in 300 ml of water was added and the mixture extracted with ether to remove the γ-vinyl-γ-butyrolactone. Acidification of the aqueous solution and extraction with ether afforded pure 3-cyclopentene-1-carboxylic acid.

EXAMPLE 2

A mixture of 52 g of 3-cyclopentene-1-carboxylic acid and excess thionyl chloride was stirred at room temperature for 1 hour. The excess thionyl chloride evaporated and the residue distilled to give 3-cyclopentene-1-carbonyl chloride, bp 52°–58° C.

The acid chloride obtained above was slowly added to an ice cooled stirred solution of 32 g of pyridine in 150 ml of ethanol. The mixture was stirred for a further hour, the ethanol evaporated and the residue treated with water and ether. The ether layer was separated, washed several times with water and dried. Evaporation of the ether left a residue of ethyl 3-cyclopentene-1-carboxylate, bp 62.5°–66° C./14 mm.

EXAMPLE 3

A solution containing 84.6 g of N-methylmorpholine N-oxide, 1 g of osmium tetroxide, 230 ml of water and 115 ml of acetone was allowed to stir for 30 minutes at room temperature. To this stirred mixture was added very slowly over at least 8 hours, a solution of 80 g of ethyl 3-cyclopentene-1-carboxylate in 115 ml of acetone. The stirred mixture was heated at 50° C. for 2 hours to complete the reaction (verified by TLC examination using ethyl acetate/hexane 70/30). Sodium bisulfite (~10 g) was added, the stirring continued for a further 15 minutes, and the mixture filtered through Celite. The pH of the filtrate was adjusted to 7 by the addition of 12 N sulfuric acid (37 ml), the acetone evaporated, the pH of the residual solution adjusted to 2 with 12 N sulfuric acid (13 ml) and the solution extracted with ethyl acetate (4×250 ml). Evaporation of the dried ethyl acetate solution gave 4-ethoxycarbonyl-1,2-cyclopentanediol.

EXAMPLE 4

A solution of 85.4 g of sodium periodate in 500 ml of water was slowly added to a stirred solution of 69 g of 4-ethoxycarbonyl-1,2-cyclopentanediol in 690 ml of tetrahydrofuran. The reaction was exothermic and cooling was necessary. After two hours a precipitate of sodium iodate was filtered off and the solution concentrated at room temperature to remove most of the tetrahydrofuran. The resulting aqueous solution contained the desired β-ethoxycarbonylglutaraldehyde and was used directly in the next reaction.

To a stirred suspension of 400 g of potassium hydrogen phthalate in 800 ml of water was added, in sequence, a solution of 80 g of acetonedicarboxylic acid in 1200 ml of water, a solution of 80 g of glycine ethyl ester hydrochloride in 400 ml of water, and finally the solution of β-ethoxycarbonylglutaraldehyde obtained above. The mixture was stirred for 20 hours at room temperature during which time carbon dioxide evolved. The mixture was basified by the addition of an excess of aqueous potassium carbonate and extracted with ethyl acetate several times. Evaporation of the dried ethyl acetate extracts gave a syrup consisting mainly of 7-ethoxycarbonyl-9-(ethoxycarbonylmethyl)-9-azabicyclo-[3.3.1]nonan-3-one.

EXAMPLE 5

Sodium borohydride (17 g) was added in small portions to a stirred solution of 87.6 g of 7-ethoxycarbonyl-9-(ethoxycarbonylmethyl)-9-azabicyclo[3.3.1]nonan-3-one in 750 ml of ethanol. The mixture was stirred overnight at room temperature, the ethanol evaporated and the residue treated with 200 ml of water. Hydrochloric acid (2 M) was added until the mixture was acid and this acid solution was immediately basified by the addition of saturated potassium carbonate solution. Extraction with ethyl acetate and evaporation of the dried extract gave a syrup which consisted mainly of 7-ethoxycarbonyl-9-(ethoxycarbonylmethyl)-9-azabicyclo[3.3.1]nonan-3-ol. The syrup can be purified by column chromatography using silica and elution with hexane-ethyl acetate (30:70).

EXAMPLE 6

A solution of 26.1 g of the crude 7-ethoxycarbonyl-9-(ethoxycarbonylmethyl)-9-azabicyclo[3.3.1]nonan-3-ol in 250 ml of methylene chloride was treated with one equivalent of methanesulfonic acid (8.42 g). The methylene chloride solution was concentrated to about 35 ml, 9.5 ml of dihydropyran was added together with one drop of methansulfonic acid, and the mixture stirred for 3 hours at room temperature. The mixture was then poured into saturated potassium carbonate solution and the product separated by extraction with ethyl acetate.

Evaporation of the dried ethyl acetate extracts gave a syrup consisting mainly of the tetrahydropyranyl ether of 7-ethoxy-carbonyl-9-(ethoxycarbonylmethyl)-9-azabicyclo[3.3.1]nonan-3-ol. It can be purified by column chromatography using silica and elution with hexane-ethyl acetate (20:80), Rf 0.7.

EXAMPLE 7

A solution of 34 g of the tetrahydropyranyl ether of 7-ethoxycarbonyl-9-(ethoxycarbonylmethyl)-9-azabicyclo-3.3.1]nonan-3-ol in 800 ml of anhydrous toluene was treated with 19 g of potassium tert-butoxide and the stirred mixture heated at 100° C. for 2 hours. Anhydrous formic acid (7.85 g) was added to the cooled mixture, the potassium formate was filtered off, and the toluene solution evaporated to give a syrup. The syrup was treated with 300 ml of 5 N hydrochloric acid and the stirred solution refluxed overnight. The cooled mixture was clarified by an extraction with methylene chloride and the aqueous acid solution evaporated to dryness. The residue was dissolved in a little water and the solution treated with a large excess of saturated potassium carbonate solution. Extraction of the resulting mixture with ethyl acetate and evaporation of the dried ethyl acetate solution gave endo-hexahydro-8-hydroxy-2,6-methano-2H-quinolizin-3(4H)-one as an oil which crystallized on standing. The base was converted to its camphorsulfonate salt, m.p. 178° C., using one equivalent of camphorsulfonic acid in ethanol.

EXAMPLE 8

A mixture of 1.8 g of endo-hexahydro-8-hydroxy-2,6-methano-2H-quinolizin-3(4H)-one, hydrofluoroboric acid (0.88 g; 60% aqueous solution) and 20 ml of ethanol was evaporated, the residue was treated with 50 ml of anhydrous toluene, and the mixture again evaporated. A stirred suspension of the anhydrous residue in 50 ml of anhydrous nitroethane at −78° C. was treated with 1.94 g of anhydrous silver tetrafluoroborate and a solution of 1.7 g of 3,5-dimethylbenzoyl chloride in 20 ml of anhydrous nitroethane was added slowly. The temperature of the stirred reaction was kept at −78° C. for 1.5 hours and then allowed to return to room temperature overnight. Triethylamine (1 g) was added, the solution filtered and the nitroethane evaporated. A solution of the residue in 20 ml of water was treated with an excess of a saturated aqueous solution of potassium carbonate and the liberated oil separated by extraction with ethyl acetate. The ethyl acetate solution was washed several times with water before being dried over magnesium sulfate and evaporated. The residue obtained was endo-8-(3,5-dimethylbenzoyl-oxy)hexahydro-2,6-methano-2H-quinolizin-3(4H)-one and this was treated with methylene chloride and ethereal hydrogen chloride to give crystals of the hydrochloride salt melting at about 291° C.

EXAMPLE 9

When the procedure of Example 8 is repeated using endo-hexahydro-8-hydroxy-2,6-methano-2H-quinolizin-3(4H)-one and the appropriate acid chloride, the corresponding esters listed below are obtained. As necessary, the acid chlorides were obtained from the appropriate carboxylic acids by standard procedures, for example, using thionyl chloride. To convert the ester to a corresponding acid salt, it was reacted with the appropriate acid with alternative solvents being used as desired.

endo-Hexahydro-8-(3-indolylcarbonyloxy)-2,6-methano-2H-quinolizin-3(4H)-one methansulfonate melting at about 278° C.

endo-8-(3-Benzofurancarbonyloxy)hexahydro-2,6-methano-2H-quinolizin-3(4H)-one endo-8-(3-Benzo[b]thiophenecarbonyloxy)hexahydro-2,6-methano-2H-quinolizin-3(4H)-one endo-8-(1-Benzyl-1H-indol-3-ylcarbonyloxy)hexahydro-2,6-methano-2H-quinolizin-3(4H)-one endo-Hexahydro-8-(1-methyl-1H-indol-3ylcarbonyloxy)-2,6-methano-2H-quinolizin-3(4H)-one endo-8-(4-Bromo-2-furylcarbonyloxy)hexahydro-2,6-methano-2H-quinolizin-3(4H)-one endo-Hexahydro-8-(5-phenyl-2-furylcarbonyloxy)-2,6-methano-2H-quinolizin-3(4H)-one endo-8-(3-Chloro-2-thienylcarbonyloxy)hexahydro-2,6-methano-2H-quinolizin-3(4H)-one endo-Hexahydro-8-(5-methyl-2-thienylcarbonyloxy)-2,6-methano-2H-quinolizin-3(4H)-one endo-Hexahydro-8-(1-methyl-1H-pyrrol-2-ylcarbonyloxy)-2,6-methano-2H-quinolizin-3(4H)-one endo-8-(3-Chloro-4-nitrobenzoyloxy)hexahydro-2,6-methano-2H-quinolizin-3(4H)-one endo-8-(3-Chloro-4-dimethylaminobenzoyloxy)hexahydro-2,6-methano-2H-quinolizin-3(4H)-one endo-8-(3,5-Dichlorobenzoyloxy)hexahydro-2,6-methano-2H-quinolizin-3(4H)-one endo-8-(3,5-Dimethoxybenzoyloxy)hexahydro-2,6-methano-2H-quinolizin-3(4H)-one endo-8-(2,5-Dimethylbenzoyloxy)hexahydro-2,6-methano-2H-quinolizin-3(4H)-one

EXAMPLE 10

Oxalyl chloride (0.76 ml) was slowly added to a stirred solution of 1 g of 5-methylindole in 20 ml of anhydrous ether at 0° C. The precipitate which formed was filtered off and dried at 80° C. to give 5-methyl-3-indolylglyoxylyl chloride.

A stirred solution of 205 mg of anhydrous silver tetrafluoroborate in 10 ml of anhydrous nitroethane was treated with a solution of 282.5 mg of endo-hexahydro-8-hydroxy-2,6-methano-2H-quinolizin-3(4H)-one tetrafluoroborate (obtained by treating the free amine with an equivalent of hydrofluoroboric acid) in 10 ml of anhydrous nitroethane at room temperature. A solution of 233 mg of 5-methyl-3-indolylglyoxylyl chloride in 10 ml of anhydrous nitroethane was slowly added and the mixture stirred at room temperature overnight. Triethylamine (101 mg) was added, the solution filtered and the nitroethane evaporated. A solution of the residue in 15 ml of water was treated with a saturated aqueous solution of potassium carbonate and the liberated oil separated by extraction with ethyl acetate. The ethyl acetate solution was washed several times with water before being dried over magnesium sulfate and evaporated. The residue was treated with methylene chloride and ethereal hydrogen chloride, and the solid filtered off and recrystallized from 2-propanol to give endo-hexahydro-8-(5-methyl-3-indolylcarbonyloxy)-2,6-methano-2H-quinolizin3(4H)-one hydrochloride.

When the above procedure was repeated using the appropriate substituted indole in place of the 5-methylindole, the following compounds were obtained:

endo-Hexahydro-8-(5-chloro-3-indolylcarbonyloxy)-2,6-methano-2H-quinolizin-3(4H)-one hydrochloride melting at about 317°–320° C. (with decomposition) after recrystallization from ethanol.

endo-Hexahydro-8-(5-cyano-3-indolylcarbonyloxy)-2,6-methano-2H-quinolizin-3(4H)-one hydrochloride melting at about 304°–305° C. (with decomposition) after recrystallization from ethanol.

endo-Hexahydro-8-(5-methoxy-3-indolycarbonyloxy)-2,6-methano-2H-quinolizin-3(4H)-one hydrochloride melting at about 303° C. (with decomposition) after recrystallization from isopropanol.

endo-Hexahydro-8-(5-methoxy-3-indolylcarbonyloxy)-2,6-methano-2H-quinolizin-3(4H)-one hydrochloride melting at about 251° C. after recrystallization from ethanol.

endo-Hexahydro-8-(6-methyl-3-indolylcarbonyloxy)-2,6-methano-2H-quinolizin-3(4H)-one oxalate melting at about 340°–342° C. after recrystallization from ethanol.

Also obtained in the same way are endo-hexahydro-8-(5-carbamoyl-3-indolylcarbonyloxy)-2,6-methano-2H-quinolizin-3(4H)-one and endo-hexahydro-8-(5-hydroxy-3-indolylcarbonyloxy)-2,6-methano-2H-quinolizin-3(4H)-one. In the later case, the starting material is 5-benzyloxyindole and the initial product is debenzylated by reduction using standard procedures.

EXAMPLE 11

Dimethylamine (40% solution in water, 0.68 g) and formaldehyde (30% solution in water, 0.49 g) were successively added to a solution of 1.25 g of endo-8-(3,5-dimethylbenzoyloxy)hexahydro-2,6-methano-2H-quinolizin-3(4H)-one in a mixture of 4 ml of ethanol and 2 ml of water. The stirred mixture was heated at 70°–75° C. for 16 hours and concentrated. Toluene (50 ml) was added and the mixture evaporated at 110° C.

A solution of the residue [which contained endo-8-(3,5-dimethylbenzoyloxy)hexahydro-4-methylene-2,6-methano-2H-quinolizin-3(4H)-one] in 30 ml of ethanol was hydrogenated at room temperature and atmospheric pressure in the presence of 0.2 g of platinum oxide (Adams catalyst). One equivalent of hydrogen was absorbed in one hour. The catalyst was filtered off, the ethanol evaporated and the residue treated with one equivalent of hydrofluoroboric acid in water. Evaporation of the aqueous solution gave a crystalline residue which was recrystallized from ethanol to give endo-8-(3,5-dimethylbenzoyloxy)hexahydro-4-methyl-2,6-methano-2H-quinolizin-3(4H)-one tetraflurorborate melting at about 270°–275° C.

EXAMPLE 12

A solution of endo-8-(3-indolylcarbonyloxy)hexahydro-2,6-methano-2H-quinolizin-3(4H)-one (1.42 g) in ethanol (5 ml) was treated with fluoboric acid (0.64 g, 60% aqueous solution) and the mixture evaporated to give endo-8-(3-indolylcarbonyloxy)-hexahydro-2,6-methano-2H-quinolizin-3(4H)-one tetrafluoroborate (1.8 g).

A stirred suspension of the above salt (1.8 g) in anhydrous nitroethane (30 ml) was treated with propane-1,3-dithiol (3 ml) and boron trifluoride etherate (3 drops) and the mixture stirred overnight at room temperature. The nitroethane was removed by evaporation and the residue triturated with ether. The solid product was filtered off, washed several times with ether, treated with water (25 ml), saturated aqueous potassium carbonate (3 ml) and ether (50 ml). The ether solution was separated off, dried (MgSO$_4$) and evaporated to give the propane dithioketal derivative, m.p. 226°–229° C. (1.6 g).

Hydrazine hydrate (3 ml) was added dropwise during one hour to a stirred refluxing solution of the above dithioketal (0.5 g) in isopropanol (20 ml) in the presence of Raney nickel (6 g, previously washed three times with isopropanol). The reflux was maintained for a further 30 minutes, the hot solution filtered through a triple superphosphate, the nickel washed several times with hot isopropanol and the combined filtrates evaporated to give endo-8-(3-indolylcarbonyloxy)-2,6-methanooctahydro-2H-quinolizine as the free base (50 mg). Addition of methylene chloride and ethereal hydrogen chloride gave the hydrochloride (30 mg), m.p. 311°–313° C. (from ethanol).

EXAMPLE 13

The procedure of Example 12 was repeated using endo-hexahydro-8-hydroxy-2,6-methano-2H-quinolizin-3(4H)-one in place of the ester. The dithioketal obtained was reduced as described in the final paragraph except that the hydrazine hydrate was left out. This gave exo-octahydro-2,6-methano-2H-quinolizin-8-ol which was then reacted with 3,5-dimethylbenzoyl chloride to give exo-8-(3,5-dimethylbenzoyloxy)octahydro-2,6-methano-2H-quinolizine which was converted to the hydrochloride, m.p. 255°–256° C.

EXAMPLE 14

A stirred mixture of 1-methyl-3-indazolylcarboxylic acid (0.31 g), thionyl chloride (2 ml) and chloroform (10 ml) was refluxed for 2 hours and the solvent was evaporated to give a residue of 1-methyl-3-indazolylcarbonyl chloride.

A stirred solution of 395 mg of anhydrous silver tetrafluoroborate in anhydrous nitroethane (10 ml) was treated with a solution of endo-hexahydro-8-hydroxy-2,6-methano-2H-quinolizin-3(4H)-one tetrafluoroborate (475 mg) in anhydrous nitroethane (10 ml) at −78° C. A solution of 1-methyl-3-indazolylcarbonyl chloride (340 mg) in anhydrous nitroethane (5 ml) was slowly added during one hour and the reaction mixture was then allowed to warm to room temperature overnight. The mixture was poured into a saturated aqueous solution of potassium carbonate (30 ml). The mixture obtained was filtered and the separated solid was washed with ethyl acetate The filtrate was then extracted twice with ethyl acetate (2×20 ml) and the solvent was evaporated from the combined ethyl acetate fractions. A solution of the residue in ethyl acetate (20 ml) was washed with water (3×15 ml) and dried over magnesium sulfate, and the solvent was evaporated to give a residual material. This material was purified by silica preparative plate chromatography using a mixture of ethanol/ethyl acetate (30:70) as eluant. The desired product compound, endo-hexahydro-8-(1-methyl-3-indazolylcarbonyloxy)-2,6-methano-2H-quinolizin-3(4H)-one, formed a band with an Rf 0.35 and was isolated by extraction with ethanol-/ethyl acetate (50:50).

EXAMPLE 15

A stirred mixture of 690 mg of endo-hexahydro-8-(3-indolylcarbonyloxy)-2,6-methano-2H-quinolizin- 3(4H)-one, 400 mg of methyl iodide, and 100 ml of acetonitrile was refluxed for 2 hours and then allowed to stand overnight at room temperature. The crystalline solid which formed was separated by filtration and dried to give endo-hexahydro-8-(3-indolylcarbonyloxy)-2,6-methano-5-methyl-3(4H)-oxo-2H-quinolizinium iodide melting at about 310°–312° C. with decomposition.

EXAMPLE 16

A mixture of 1.84 g of 4-quinolinecarboxylic acid, 25 ml of methylene chloride and trifluoroacetic anhydride was stirred at room temperature for 5 minutes and then cooled to 0° C. A mixture of 1.92 g of endo-hexahydro-8-hydroxy-2,6-methano-2H-quinolizin-3(4)-one, 1.2 g of trifluoroacetic acid, 25 ml of methylene chloride and 20 ml of tetrahydrofuran was slowly added and the mixture stirred at room temperature for 20 hours. The solid present was removed by filtration and the filtrate was basified by the addition of aqueous potassium carbonate. The resulting basic solution was extracted with ethyl acetate and the ethyl acetate extract was dried and filtered. The solvent was then evaporated to give residual material which was treated with ether and ethereal hydrogen chloride to give endo-hexahydro-8-(4-quinolinylcarbonyloxy)-2,6-methano-2H-quinolizin-3(4H)-one hydrochloride melting at about 302° C. (dec) after recrystallization from ethanol.

EXAMPLE 17

A solution of endo-8-(3-indolylcarbonyloxy)hexahydro-2,6-methano-2H-quinolizin-3(4H)-one (50 mg) in 1 ml of ethanol was added dropwise to 20 mg of sodium borohydride in 1 ml of ethanol at room temperature. The reaction was then quenched by the addition of 2 ml of saturated aqueous ammonium chloride solution. The aqueous mixture was extracted three times with ethyl acetate and the solvent was evaporated from the combined organic extracts under nitrogen. This gave a solid residue which was endo-8-(3-indolylcarbonyloxy)-2,6-methanooctahydro-2H-quinolizin-3-ol.

EXAMPLE 18

Oxalyl chloride (10 ml) was slowly added to a stirred solution of 11.7 g of indole in 50 ml of anhydrous ether at 0° C. The temperature was allowed to reach room temperature and the mixture stirred for a further 2 hours. The orange precipitate was filtered off, washed with anhydrous ether and dried at 50° C. to give 3-indolylglyoxylyl chloride.

A suspension of 6.42 g of silver tetrafluoroborate in 300 ml of anhydrous toluene was evaporated to dryness to give a residue of the anhydrous salt. A solution of this anhydrous salt in anhydrous nitroethane (50 ml) was slowly added to a stirred solution of 7.74 g of trans-hexahydro-8-hydroxy-2,6-methano-2H-quinolizin-3(4H)-one tetrafluoroborate and 6 g of 3-indolylglyoxylyl chloride in 100 ml of anhydrous nitroethane cooled to −10° C. under nitrogen. The mixture was stirred overnight at room temperature, poured into a saturated aqueous solution of potassium carbonate (30 ml) and the resulting mixture was extracted with 200 ml of ethyl acetate. The separated organic phase was dried over magnesium sulfate, the solvent evaporated and the residue redissolved in 200 ml of ethyl acetate. After washing three times with water to remove unchanged starting alcohol, the ethyl acetate solution was dried and evaporated to give a residue (7.4 g) of crude trans-hexahydro-8-(3-indolylcarbonyloxy)-2,6-methano-2H-quinolizin-3(4H)-one base. The residue was treated with a solution of 2.2 g of methanesulphonic acid in 50 ml of ethanol at 60° C. The solid material remaining undissolved was filtered off and the reddish-brown solution was treated with charcoal. On cooling, the filtered solution afforded crystals of trans-hexahydro-8-(3-indolylcarbonyloxy)-2,6-methano-2H-quinolizin-3(4H)-one methanesulphonate monohydrate (66%).y standard procedures.

We claim:

1. A pharmaceutical composition suitable for use in the treatment of anxiety, psychosis, glaucoma, and for stimulating gastric motility comprising a pharmaceutically acceptable carrier in admixture with a compound of the formula

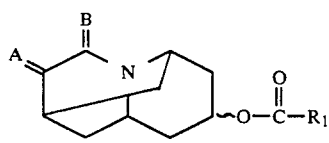

wherein A is $H_2$, O, (H)(OH), $(OH)_2$ or N—OH; B is $H_2$, $(H)(CH_3)$, $(H)(CH_2NR_3R_4)$ or $CH_2$ wherein $R_3$ and $R_4$ are $C_{2-4}$ alkyl or are combined to give tetramethylene, pentamethylene or —$CH_2CH_2$—O—$CH_2CH_2$; $R_1$ is

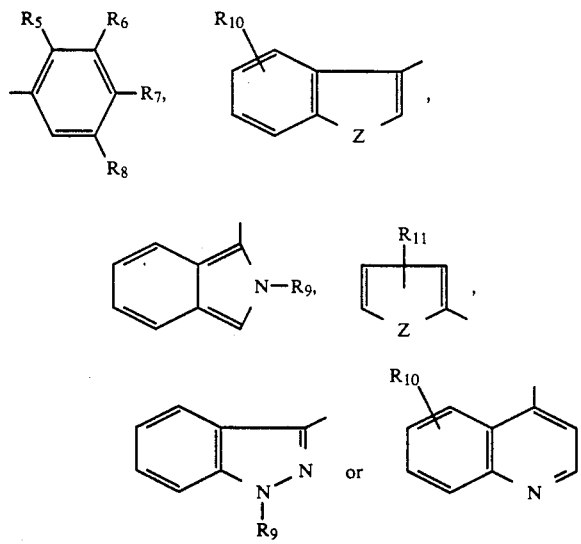

wherein Z is $NR_9$, O or S; $R_5$, $R_6$ and $R_8$ are each hydrogen, halogen, $C_{1-3}$ alkyl or $C_{1-3}$ alkoxy; $R_7$ is hydrogen, amino, $(C_{1-4}$ alkyl)amino, $(C_{1-4}$ alkyl)$_2$amino, alkoxy, or nitro; $R_9$ is hydrogen, $C_{1-4}$ alkyl or phenyl $(C_{1-2}$ alkyl); $R_{10}$ is hydrogen, halogen, $C_{1-4}$ alkyl, $C_{1-4}$ alkoxy, hydroxyl, cyano or —$CONH_2$; $R_{11}$ is hydrogen, halogen, $C_{1-4}$ alkyl or phenyl; the wavy line indicates that the configuration of the oxygen substituent on the ring can be endo or exo; and the pharmaceutically acceptable acid addition and quarternary ammonium salts of the aforesaid compounds.

2. A pharmaceutical composition according to claim 1 wherein said compound is endo-hexahydro-8-(3-indolylcarbonyloxy)-2,6-methano-2H-quinolizin-3(4H)-one.

3. A method for the treatment of anxiety comprising administering to a patient in need thereof of an effective amount of a compound of the formula

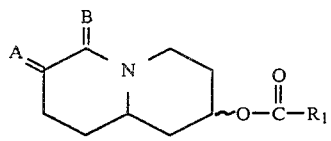

wherein A is $H_2$, O, (H)(OH), $(OH)_2$ or N—OH; B is $H_2$, $(H)(CH_3)$, $(H)(CH_2NR_3R_4)$ or $CH_2$ wherein $R_3$ and $R_4$ are $C_{2-4}$ alkyl or are combined to give tetramethylene, pentamethylene or —$CH_2CH_2$—O—$CH_2CH_2$—; $R_1$ is

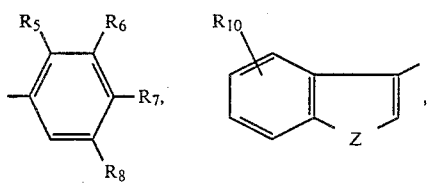

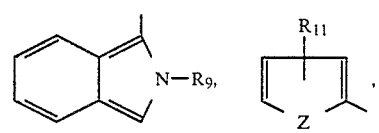

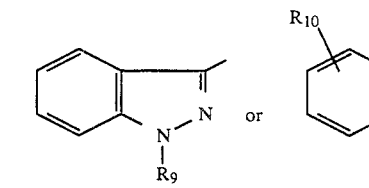

wherein Z is $NR_9$, O or S; $R_5$, $R_6$ and $R_8$ are each hydrogen, halogen, $C_{1-3}$ alkyl or $C_{1-3}$ alkoxy; $R_7$ is hydrogen, amino, ($C_{1-4}$ alkyl)amino, ($C_{1-4}$ alkyl)$_2$amino, alkoxy or nitro; $R_9$ is hydrogen, $C_{1-4}$ alkyl or phenyl ($C_{1-2}$ alkyl); $R_{10}$ is hydrogen, halogen, $C_{1-4}$ alkyl, $C_{1-4}$ alkoxy, hydroxy, cyano or —$CONH_2$; $R_{11}$ is hydrogen, halogen, $C_{1-4}$ alkyl or phenyl; the wavy line indicates that the configuration of the oxygen substituent on the ring can be endo or exo; and the pharmaceutically acceptable acid addition and quarternary ammonium salts of the aforesaid compounds.

4. A method according to claim 3 wherein said compound is endo-hexahydro-8-(3-indolylcarbonyloxy)-2,6-methano-2H-quinolizin-3(4H)-one.

5. A method for the treatment of psychosis comprising administering to a patient in need thereof an effective amount of a compound of the formula

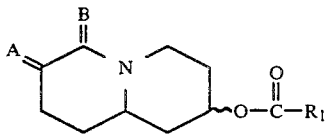

wherein A is $H_2$, O, (H)(OH), $(OH)_2$ or N—OH; B is $H_2$, $(H)(CH_3)$, $(H)(CH_2NR_3R_4)$ or $CH_2$ wherein $R_3$ and $R_4$ are $C_{2-4}$ alkyl or are combined to give tetramethylene, pentamethylene or —$CH_2CH_2$—O—$CH_2CH_2$—; $R_1$ is

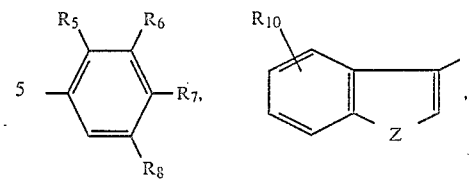

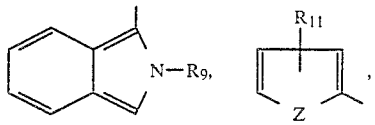

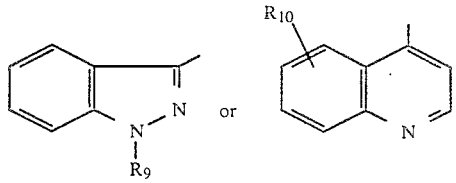

wherein Z is $NR_9$, O or S; $R_5$, $R_6$ and $R_8$ are each hydrogen, halogen, $C_{1-3}$ alkyl or $C_{1-3}$ alkoxy; $R_7$ is hydrogen, amino, ($C_{1-4}$ alkyl)amino, ($C_{1-4}$ alkyl)$_2$amino, alkoxy or nitro; $R_9$ is hydrogen, $C_{1-4}$ alkyl or phenyl ($C_{1-2}$ alkyl); $R_{10}$ is hydrogen, halogen, $C_{1-4}$ alkyl, $C_{1-4}$ alkoxy, hydroxy, cyano or —$CONH_2$; $R_{11}$ is hydrogen, halogen, $C_{1-4}$ alkyl or phenyl; the wavy line indicates that the configuration of the oxygen substituent on the ring can be endo or exo; and the pharmaceutically acceptable acid addition and quarternary ammonium salts of the aforesaid compounds.

6. A method according to claim 5 wherein said compound is endo-hexahydro-8-(3-indolylcarbonyloxy)-2,6-methano-2H-quinolizin-3(4H)-one.

7. A method for stimulating gastric motility comprising administering to a patient in need thereof an effective amount of a compound of the formula:

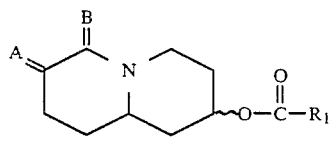

wherein A is $H_2$, O, (H)(OH), $(OH)_2$ or N—OH; B is $H_2$, $(H)(CH_3)$, $(H)(CH_2NH_3R_4)$ or $CH_2$ wherein $R_3$ and $R_4$ are $C_{2-4}$ alkyl or are combined to give tetramethylene, pentamethylene or —$CH_2CH_2$—O—$CH_2CH_2$—; $R_1$ is

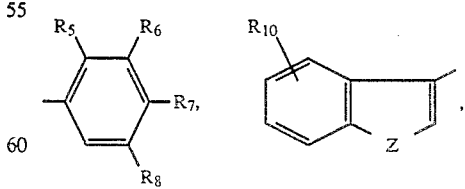

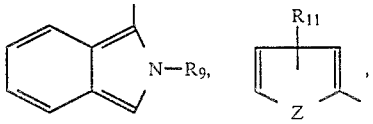

-continued

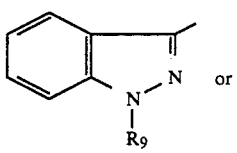 or 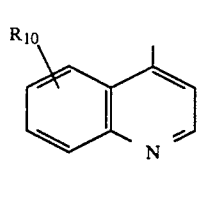

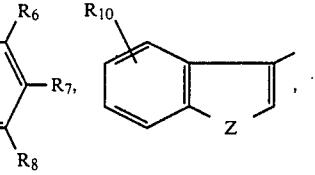

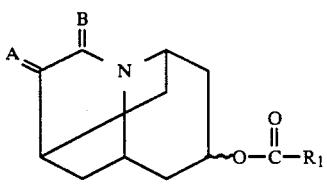

wherein Z is $NR_9$, O or S; $R_5$, $R_6$ and $R_8$ are each hydrogen, halogen, $C_{1-3}$ alkyl or $C_{1-3}$ alkoxy; $R_7$ is hydrogen, amino, ($C_{1-4}$ alkyl)amino, ($C_{1-4}$ alkyl)$_2$amino, alkoxy or nitro; $R_9$ is hydrogen, $C_{1-4}$ alkyl or phenyl ($C_{1-2}$ alkyl); $R_{10}$ is hydrogen, halogen, $C_{1-4}$ alkyl, $C_{1-4}$ alkoxy, hydroxy, cyano or —$CONH_2$; $R_{11}$ is hydrogen, halogen, $C_{1-4}$ alkyl or phenyl; the wavy line indicates that the configuration of the oxygen substituent on the ring can be endo or exo; and the pharmaceutically acceptable acid addition and quarternary ammonium salts of the aforesaid compounds.

8. A method according to claim 7 wherein said compound is endo-hexahydro-8-(3-indolylcarbonyloxy)-2,6-methano-2H-quinolizin-3(4H)-one.

9. A method for the treatment of glaucoma comprising administering to a patient in need thereof an effective amount of a compound of the formula:

wherein A is $H_2$, O, (H)(OH), (OH)$_2$ or N—OH; B is $H_2$, (H)(CH$_3$), (H)(CH$_2$NR$_3$R$_4$) or CH$_2$ wherein $R_3$ and $R_4$ are $C_{2-4}$ alkyl or are combined to give tetramethylene, pentamethylene or —$CH_2CH_2$—O—$CH_2CH_2$—; $R_1$ is wherein Z is $NR_9$, O or S; $R_5$, $R_6$ and $R_8$ are each hydrogen, halogen, $C_{1-3}$ alkyl or $C_{1-3}$ alkoxy; $R_7$ is hydrogen, amino, ($C_{1-4}$ alkyl)amino, ($C_{1-4}$ alkyl)$_2$amino, alkoxy or nitro; $R_9$ is hydrogen, $C_{1-4}$ alkyl or phenyl ($C_{1-2}$ alkyl); $R_{10}$ is hydrogen, halogen, $C_{1-4}$ alkyl, $C_{1-4}$ alkoxy, hydroxy, cyano or —$CONH_2$; $R_{11}$ is hydrogen, halogen, $C_{1-4}$ alkyl or phenyl; the wavy line indicates that the configuration of the oxygen substituent on the ring can be endo or exo; and the pharmaceutically acceptable acid addition and quarternary ammonium salts of the aforesaid compounds.

10. A method according to claim 9 wherein said compound is endo-hexahydro-8-(3-indolylcarbonyloxy)-2,6-methano-2H-quinolizin-3(4H)-one.

11. A pharmaceutical composition according to claim 1 wherein said compound is endo-8-(3-indolylcarbonyloxy)-2,6-methanooctahydro-2H-quinolizin-3-ol.

12. A method according to claim 3 wherein said compound is endo-8-(3-indolylcarbonyl-oxy)-2,6-methanooctahydro-2H-quinolizin-3-ol.

13. A method according to claim 5 wherein said compound is endo-8-(3-indolylcarbonyl-oxy)-2,6-methanooctahydro-2H-quinolizin-3-ol.

14. A method according to claim 7 wherein said compound is endo-8-(3-indolylcarbonyl-oxy)-2,6-methanooctahydro-2H-quinolizin-3-ol.

15. A method according to claim 9 wherein said compound is endo-8-(3-indolylcarbonyl-oxy)-2,6-methanooctahydro-2H-quinolizin-3-ol.

* * * * *

UNITED STATES PATENT AND TRADEMARK OFFICE
CERTIFICATE OF CORRECTION

PATENT NO. : 5,011,846
DATED : April 30, 1991
INVENTOR(S) : Maurice W. Gittos et al., It is certified that error appears in the above-identified patent and that said Letters Patent is hereby corrected as shown below:

At column 1, line 64, the patent reads "-CONH$_2$; indicates" and should read -- -CONH$_2$; R$_{11}$ is hydrogen, halogen, C$_{1-4}$ alkyl or phenyl; the wavy line indicates --

At column 1, line 25, the patent reads

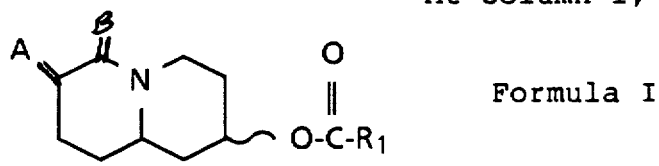

Formula I and should read

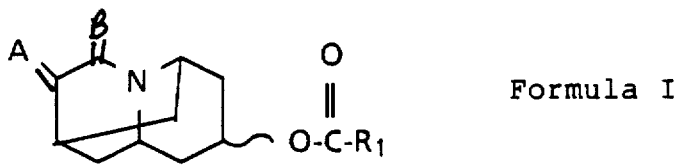

Formula I

At column 2, line 5, the patent reads

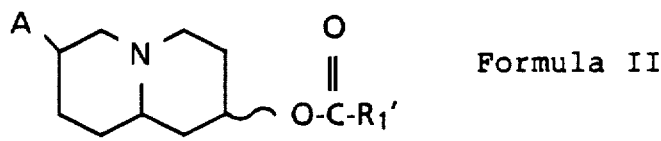

Formula II and should read

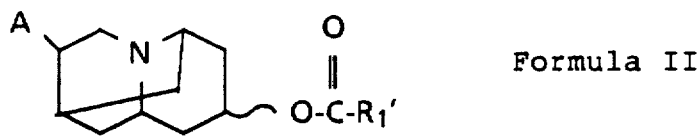

Formula II

At column 2, line 52, the patent reads "2-naphthalensulfonic" and should read -- 2-naphthalenesulfonic --.

UNITED STATES PATENT AND TRADEMARK OFFICE
CERTIFICATE OF CORRECTION

PATENT NO. : 5,011,846
DATED : April 30, 1991
INVENTOR(S) : Maurice W. Gittos et al., It is certified that error appears in the above-identified patent and that said Letters Patent is hereby corrected as shown below:

At column 3, line 26, the patent reads "or a reactive derivatives" and should read -- or reactive derivatives".
At column 3, line 30, the patent reads

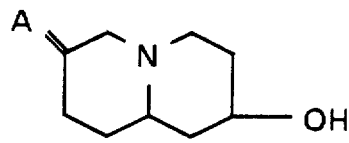

and should read

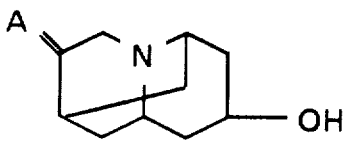

At column 4, lines 53-54, the patent reads "by a Mannich reactions" and should read --by a Mannich reaction--. At column 5, lines 40-41, the patent reads "of a medicaments, therefor." and should read --of medicaments therefor.--. At column 6, line 36, the patent reads "warmblooded" and should read --warm-blooded--

At column 7, line 4, the patent reads "carier" and should read --carrier--. At column 7, line 27, the patent reads "Therefor," and should read --Therefore,--. At column 7, line 64, the patent reads "Sterotazic" and should read -- Stereotaxic--, At column 8, line 47, the patent reads "administerd" and should read --administered--. At column 8, line 57, the patent reads "a patients glaucoma" and should read --a patient's glaucoma--. At column 13, line 4, the patent reads "methansulfonic" and should read --methanesulfonic--.

UNITED STATES PATENT AND TRADEMARK OFFICE
CERTIFICATE OF CORRECTION

PATENT NO. : 5,011,846

DATED : April 30, 1991

INVENTOR(S) : Maurice W. Gittos et al.,

It is certified that error appears in the above-identified patent and that said Letters Patent is hereby corrected as shown below:

At column 14, line 68, the patent reads "quinolizin3(4H)" and should read --quinolizin-3(4H)--

At column 16, line 52, the patent reads "acetate The" and should read --acetate. The--, At column 18, Claim 1, line 29, the patent reads "-CH₂CH₂-O-CH₂CH₂;" and should read -- -CH₂CH₂-O-CH₂CH₂-; --

At column 18, Claim 1, line 59, the patent reads "hydroxyl," and should read --hydroxy,--

At column 19, claim 3, line 5, at column 19, line 57, and again at column 20, line 42, the patent reads

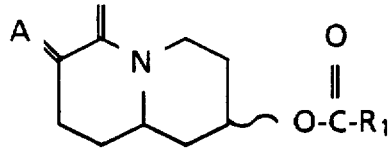

and should read

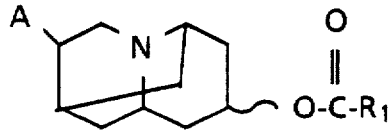

UNITED STATES PATENT AND TRADEMARK OFFICE
CERTIFICATE OF CORRECTION

PATENT NO. : 5,011,846

DATED : April 30, 1991

INVENTOR(S) : Maurice W. Gittos et al.,

It is certified that error appears in the above-identified patent and that said Letters Patent is hereby corrected as shown below:

At column 20, line 50, the patent reads "$(CH_2NH_3R_4)$" and should read -- $(CH_2NR_3R_4)$ --

Signed and Sealed this

Twenty-eighth Day of April, 1992

*Attest:*

HARRY F. MANBECK, JR.

*Attesting Officer*      *Commissioner of Patents and Trademarks*